United States Patent [19]

Hori et al.

[11] Patent Number: 5,116,829
[45] Date of Patent: May 26, 1992

[54] STEROID COMPOUNDS

[75] Inventors: Kimihiko Hori, Utsunomiya; Yasuto Suzuki; Tomoki Morioka, both of Ichikai; Shigeru Moriwaki, Utsunomiya; Osamu Hirota, Ichikai; Shuichi Tsuchiya, Utsunomiya, all of Japan

[73] Assignee: Kao Corporation, Tokyo, Japan

[21] Appl. No.: 683,346

[22] Filed: Apr. 10, 1991

[30] Foreign Application Priority Data

Apr. 23, 1990 [JP] Japan .................. 2-107255

[51] Int. Cl.$^5$ .............. A61K 31/58; C07J 71/00; C07J 7/00
[52] U.S. Cl. .................. 514/172; 514/180; 514/174; 514/179; 552/581; 540/67
[58] Field of Search .............. 552/581; 514/180, 172, 514/174, 179; 540/67

[56] References Cited

U.S. PATENT DOCUMENTS 2,814,632  11/1957  Nussbaum .............. 552/581
4,014,909  3/1977  Torossian et al. .............. 552/581

FOREIGN PATENT DOCUMENTS 2105724  3/1983  United Kingdom .............. 552/581

Primary Examiner—Alan Siegel
Assistant Examiner—Kimberly J. Kestler
Attorney, Agent, or Firm—Oblon, Spivak, McClelland, Maier & Neustadt

[57] ABSTRACT

A 21-substituted steroid compound is disclosed. The compound has a structure of formula (I),

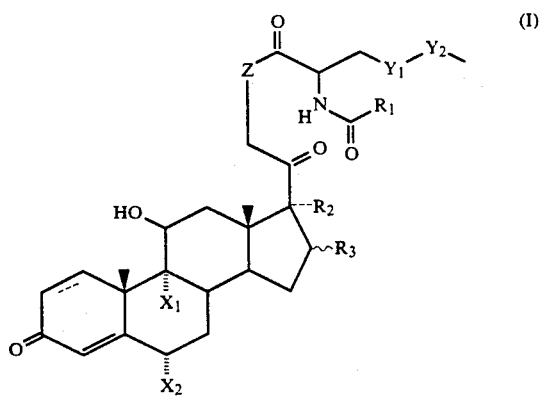

wherein $R^1$ is a hydrogen atom, a lower alkyl, lower alkenyl, lower alkoxy, or phenyl group, $R^2$ is a hydroxyl group or an acyloxy group having 1-6 carbon atoms, $R^3$ is a hydrogen atom or a lower alkyl group, or $R^2$ and $R^3$ may together form a lower alkylidenedioxy group, $X^1$ and $X^2$ may be the same or different and individually represents a hydrogen atom or a halogen atom, $Y^1$ and $Y^2$ may be the same or different and individually represents a methylene group or a sulfur atom, Z is a sulfur atom or an imino group, the wave line means that the configuration of $R^3$ may be of either α or β, and dotted line between the 1 and 2 position means that the bond may be the double bond. It has excellent anti-inflammatory, anti-allergic and anti-asthma activities with little side effects, and is useful for the prevention, cure, and treatment of on inflammation, allergic diseases, rheumatism, and the like.

7 Claims, 2 Drawing Sheets

STEROID COMPOUNDS

BACKGROUND OF THE INVENTION

1. Field of the Invention

The present invention relates to novel steroid compounds.

2. Description of the Background Art

Steroid compounds are very important drugs which are essential for the treatment and the cure of skin diseases and allergic diseases such as bronchial asthma, and rheumatism, etc. They are widely applicable to all allergic and inflammatory diseases, including, for example, contact dermatitis, atopic dermatitis, seborrheic dermatitis, eczema nummulare, lichen simplex chronicus Vidal, housewive's eczema, prurigo, drug eruption, toxicodermia, psoriasis, pustulosis palmaris et plantaris, lichen planus, lichen nitidus, pityriasis rubra pilaris, pityriasis rosea Gibert, erythema-group, erythroderma, discoid lupus erythematosus, pemphigus, pemphigoid, Duhring dermatitis herpetiformis, alopecia areata, vitiligo vulgaris, sarcoidosis, keloid, hypertrophic scar, hypoadrenalism, rheumatism, bronchial asthma, ulcerous intestinitis, allergic rhinitis, conjunctivitis, and the like.

Many of the patients to whom these steroid compounds are to be administered are those suffering from intractable inflammation, allergic diseases, or rheumatism, requiring the treatment in wide and various parts of the body extending over a long period of time. In spite of doctor's efforts in designing and advising the manner in which the steroid drugs are administered, e.g. encapsulation, so as to prevent the side effects of the drug, the problem of side effects remains still to be solved. Such side effects include, for example, localized ones, e.g. dermal atrophy, steroid acne, steroid rosacea, depigmentation, etc., as well as those systemic, extending over the whole body of the patient, e.g. cushingoid signs, infant hypoevolutism, infectious diseases, osteoporosis, etc. in the internal medicine.

Steroid compounds substituted by acylthio groups derived from thiol carboxylic acid are reported to decrease the risks of the side effects (Japanese Patent Application Laid-open (kokai) Nos. 79399/1980, 26899/1983, 48999/1985, 36273/1976, etc.). These compounds, however, are not always satisfactory in their rather weak pharmacological activity and insufficient effects in reducing the side effects.

Development of a steroid compound is therefore awaited which possesses pharmacological activity strong enough to permit fast cure of the intractable inflammation, allergic diseases, or rheumatism without side effects.

SUMMARY OF THE INVENTION

In view of this situation, the present inventors have undertaken extensive studies and found that a steroid compound of formula (I) hereinafter in which the 21 position of the steroid structure is substituted by acylthio or amide group derived from N-acylamino acid exhibited an excellent pharmacological activity against inflammation, allergic diseases, or rheumatism, and the like without minimal side effects. This finding has led to the completion of the present invention.

Accordingly, an object of the present invention is to provide a 21-substituted steroid compound of formula (I), wherein $R^1$ is a hydrogen atom, a lower alkyl, lower alkoxy, or phenyl group, $R^2$ is a hydroxyl group or an acyloxy group having 1-6 carbon atoms, $R^3$ is a hydrogen atom or a lower alkyl group, or $R^2$ and $R^3$ may together form a lower alkylidenedioxy group, $X^1$ and $X^2$ may be the same or different and individually represents a hydrogen atom or a halogen atom, $Y^1$ and $Y^2$ may be the same or different and individually represents a methylene group or a sulfur atom, Z is a sulfur atom or an imino group, the wave line means that the configuration of $R^3$ may be of either $\alpha$ or $\beta$, and dotted line between the 1 and 2 position mearns that the bond may be the double bond.

Another object of the present invention is to provide a pharmaceutical composition for curing inflammation (especially external application), allergic diseases (e.g. bronchial asthma, allergic rhinitis, etc.), or rheumatism, or for an eye drop comprising an effective amount of the above steroid compound and a pharmaceutically acceptable carrier.

Other and further objects, features and advantages of this invention will appear more fully from the following description.

DETAILED DESCRIPTION OF THE INVENTION AND PREFERRED EMBODIMENTS

Examples of lower alkyl groups which are represented by $R^1$ and $R^2$ in formula (I) include linear or branched alkyl groups having 1-5 carbon atoms, e.g. methyl, ethyl, n-propyl, isopropyl, n-butyl, t-butyl, or amyl groups. A lower alkoxy group which is represented by $R^1$ may be a linear or branched alkoxy groups having 1-5 carbon atoms, e.g. methoxy, ethoxy, n-propyloxy, 2-propyloxy, n-butyloxy, t-butyloxy, or pentyloxy group. As examples of an acyloxy group having 1-6 carbon atoms, which is represented by $R^2$, e.g. formyloxy, acetoxy, propionyloxy, butanoyloxy, pentanoyloxy, and hexanoyloxy groups are given. Isopropylidenedioxy group, 3-pentylidenedioxy group, and the like may be the lower alkylidenedioxy groups which can be formed together by $R^2$ and $R^3$. Chlorine, florine, bromine, and iodine are typical examples of the halogen atom represented by $X^1$ and $X^2$. 21-Substituted steroid compounds of formula (I) of the present invention can be prepared, for example, by reacting 21-mercapto (or amino) steroid of formula (II) and an N-acylamino acid of formula (III) in the presence of a suitable condensing agent according to the following reaction scheme.

tate, N,N-dimethylformamide, or the like may be used so far as it is inert to the reaction.

The 21-substituted steroid compounds of formula (I) prepared in this manner can be separated from the reaction mixture and purified by a known method, e.g. column chromatography, recrystallization, and the like.

The 21-substituted steroid compounds of formula (I) thus prepared exhibits an excellent pharmacological activity against inflammation, allergic diseases, or rheumatism, and the like without minimal side effects, and effective as an active component of pharmaceutical compositions for curing inflammation, allergic diseases, wherein $R^1$, $R^2$, $R^3$, $X^1$, $X^2$, $Y^1$, $Y^2$, and Z have the same meanings as defined previously for formula (I). 21-Mercapto steroid of formula (II) can be prepared by a known method, e.g. the method described in Japanese Patent Publication (kokoku) Nos. 40470/1974, 42080/1982, Japanese Patent Application Laid-open (kokai) Nos. 215695/1988, 303994/1988, and the like. 21-Amino steroid of formula (II) can be prepared by a known method, e.g. the method described in U.S. Pat. No. 3,020,275 and the like.

The reaction for the preparation of compound (I) may be carried out using 1-10 moles of N-acylamino acid of formula (III) per one mole of 21-mercapto (or amino) steroid of formula (II) in the presence of 1-10 moles of condensing agent and, optionally, a basic catalyst, in a solvent at a temperature of −10° C. to 100° C., preferably 10° to 50° C.

As a condensing agent, N,N'-dicyclohexylcarbodiimide, N,N'-dicyclohexylcarbodiimide with N-hydroxysuccinimide, N,N'-dicyclohexylcarbodiimide with 1-hydroxybenzotriazol or the like can be used. Examples of the basic catalyst are 4-pyrrodinopyridine, dimethylaminopyridine, pyridine, triethylamine, and the like. Any solvent, e.g. methylene chloride, ethyl aceor rheumatism, or for an eye drop.

They are given to the patient by oral administration, by intravenous or locallized injection, or by external application.

When the 21-substituted steroid compound of formula (I) is used as an active component of an agent for external application, the composition is prepared into various forms, e.g. liquid preparations, oil preparations, lotion, liniment, oil-based ointments, emulsion-based ointments, water-soluble ointments, pastas, plasters, cataplasm, etc. Pharmacologically and pharmaceutically acceptable base components, solubility adjuvants, solubilizers, stabilizers, surfactants, and the like can be incorporated into these preparation.

A preferable concentration of the 21-substituted steroid compound of formula (I) in the anti-inflammatory composition for external application is in the range of 0.01-2.00% by weight, and preferably 0.1-1.0% by weight. This composition is usually applied to the portion of the disease one time or several times a day.

Even though it is possible that the 21-substituted steroid compound of formula (I) is used as the active component of an anti-allergic composition for oral administration, more preferable forms are those for non-oral administration, such as nasal drips, inhalation preparations, and the like. Any pharmacologically and pharmaceutically acceptable base components, solubilizers, solubility adjuvants, stabilizers, sweetners, perfumes, surfactants, and the like can be incorporated into these preparation. A preferable form of the inhalation preparations is a spray type in which the active component is filled in a pressure container together with a carrier gas such as flon gas or the like. Such an anti-allergic agent is preferably given one time or several times a day, with a preferable dose of the 21-substituted steroid compound of formula (I) per day being 0.1-50 mg, although this amount can be varied depending on the body weight, age, sex, the manner of the administration, and the symptom of the patient.

Either oral or nonoral type of administration is possible for the composition for curing rheumatism comprising the 21-substituted steroid compound of formula (I), but nonoral form, especially injection, is preferable. In the preparation of such oral or nonoral type antirheumatism compositions, in addition to the 21-substituted steroid compound of formula (I) which is the active component any parmacologically and pharmaceutically acceptable base components, solubilizers, solubility adjuvants, stabilizers, sweetners, perfumes, surfactants, and the like can be incorporated. Such an anti-rheumatism agent is preferably given one time or several times a day, with a preferable dose of the 21-substituted steroid compound of formula (I) per day being 1-200 mg, although this amount can be varied depending on the body weight, age, sex, the manner of the administration, and the symptom of the patient.

A liquid eye drop or an ointment eye treatment composition is suitable form of the preparation comprising the 21-substituted steroid compound of formula (I). They can be prepared by incorporating any parmacologically and pharmaceutically acceptable base components, solubilizers, solubility adjuvants, stabilizers, sweeteners, perfumes, surfactants, and the like can be incorporated. Such a composition for the eye treatment is preferably given one time or several times a day, with a preferable dose of the 21-substituted steroid compound of formula (I) per day being 0.1-50 mg, although this amount can be varied depending on the body weight, age, sex, the manner of the administration, and the symptom of the patient.

Other features of the invention will become apparent in the course of the following description of the exemplary embodiments which are given for illustration of the invention and are not intended to be limiting thereof.

EXAMPLES

Synthetic Example 1

9-Fluoro-21-[2-(formylamino)-4-methylthio-1-oxobutylthio]-11β,17-dihydroxy-16β-methylpregna-1,4-diene-3,20-dione (Compound No. 1)

To a stirred solution of of N-formyl-L-methionine (7.8 gm) in dry ethyl acetate (120 ml) were added 9-fluoro-11β,17-dihydroxy-16β-methylpregna-1,4-diene-3,20-dione-21-thiol (6.0 gm) in dry ethyl acetate (100 ml) and dicyclohexylcarbodiimide (18.2 gm) in dry ethyl acetate (100 ml) at room temperature. The reaction mixture was stirred at room temperature for for 4 hours.

The resulting reaction mixture was filtrated to remove precipitate. The organic layer was washed with distilled water and then with saturated brine, and dried over anhydrous sodium sulfate. The solvent was evaporated and the residue was purified by column chromatography on silicagel using chloroform-methanol as an eluent. After evaporation of the solvent, the residue was crystallized from acetone-n-hexane to give 3.66 gm of the title compound. NMR (DMSO-d$_6$)δ; 0.86–2.80 (m, 15H), 0.92 (s, 3H), 0.99 (d, 3H, J=7Hz), 1.49 (s, 3H), 2.05 (s, 3H), 3.94 (d, 1H, J=18Hz), 4.17 (d, 1H, J=18Hz), 4.18 (s, 1H), 4.62 (m, 1H), 5.28 (s, 1H), 5.48 (s, 1H), 6.01 (s, 1H), 6.22 (d, 1H, J=10Hz), 7.29 (d, 1H, J=10Hz), 8.18 (s, 1H), 8.84 (d, 1H, J=8Hz)

IRνmax (cm$^{-1}$); 3384, 2936, 1666, 1622, 1522, 1454, 1392, 1300, 1048, 894, 710.

Synthetic Example 2

9-Fluoro-21-[2-(formylamino)-4-methylthio-1-oxobutylthio]-11β,17-dihydroxy-16β-methylpregna-1,4-diene-3,20-dione (Compound No. 1)

To a stirred solution of N-formyl-L-methionine (11.13 gm) in dry ethyl acetate (200 ml) were added 1-hydroxybenzotriazol (9.71 gm) in dry ethyl acetate (100 ml) and dicyclohexylcarbodiimido (16.43 gm) in dry ethyl acetate (100 ml) each at room temperature. The reaction mixture was stirred for 1.5 hours. To the stirred reaction mixture was added dropwise a solution of 9-fluoro-11β,17-dihydroxy-16β-methylpregna-1,4-diene-3,20-dione-21-thiol (12.95 gm) and triethylamine (35 ml) in dry ethyl acetate (600 ml) at 0° C. for 1 hour. The reaction mixture was stirred at room temperature for 4.5 hours. The title compound (15.68 gm) was prepared by purifying the resulting reaction mixture in the same manner as in Synthetic Example 1.

Synthetic Example 3

9-Chloro-21-[2-(formylamino)-4-methylthio-1-oxobutylthio]-11β,17-dihydroxy-16β-methylpregna-1,4-diene-3,20-dione (Compound No. 2)

The title compound (0.51 gm) was prepared from 9-chloro-11β,17-dihydroxy-16β-methylpregna-1,4-diene-3,20-dione-21-thiol (0.85 gm) and N-formyl-L-methionine (1.15 gm) in the same manner as in Synthetic Example 1.

NMR (DMSO-d$_6$)δ; 0.93 (s, 3H), 1.01 (d, 3H, J=7Hz), 1.10–2.73 (m, 15H), 1.61 (s, 3H), 2.05 (s, 3H), 3.94 (d, 1H, J=18Hz), 4.17 (d, 1H, J=18Hz), 4.35 (s, 1H), 4.61 (m, 1H), 5.43 (d, 1H, J=4Hz), 5.50 (s, 1H), 5.98 (s, 1H), 6.21 (d, 1H, J=10Hz), 7.30 (d, 1H, J=10Hz), 8.18 (s, 1H), 8.82 (d, 1H, J=8Hz)

IRνmax (cm$^{-1}$); 3368, 2932, 1662, 1618, 1526, 1392, 1298, 1044, 888, 716.

Synthetic Example 4

9-Fluoro-21-[2-(formylamino)-4-methylthio-1-oxobutylthio]-11β-hydroxy-16α,17α-isopropylidenedioxypregna-1,4-diene-3,20-dione (Compound No. 3)

To a stirred solution of N-formyl-L-methionine (1.9 gm) in dry methylene chloride (70 ml) were added 9-fluoro-11β-hydroxy-16α,17α-isopropylidenedioxypregna-1,4-diene- 3,20-dione-21-thiol (1.5 gm) in dry methylene chloride (70 ml) and dicyclohexylcarbodiimide (4.1 gm) in dry methylene chloride (60 ml) at room temperature. The reaction mixture was stirred at room temperature for 4 hours. The title compound (0.28 gm) was prepared by purifying the resulting reaction mixture in the same manner as in Synthetic Example 1.

NMR (CDCl$_3$)δ; 0.90 (s, 3H), 1.17 (s, 3H), 1.31–2.75 (m, 14H), 1.44 (s, 3H), 1.55 (s, 3H), 2.14 (s, 3H), 3.90 (d,

1H, J=17Hz), 4.16 (d, 1H, J=17Hz), 4.42 (m, 1H), 4.91 (m, 1H), 4.96 (s, 1H), 4.98 (s, 1H), 6.13 (s, 1H), 6.34 (d, 1H, J=10Hz), 6.67 (d, 1H, J=8Hz), 7.23 (d, 1H, J=10Hz), 8.28 (s, 1H).

IRνmax (cm$^{-1}$); 3384, 2940, 1666, 1622, 1444, 1386, 1300, 1060, 898, 542.

Synthetic Example 5

9-Fluoro-21-[2-(formylamino)-4-methylthio-1-oxobutylthio]-11β,17-dihydroxy-16α-methylpregna-1,4-diene-3,20-dione (Compound No. 4)

The title compound (0.34 gm) was prepared from 9-fluoro-11β,17-dihydroxy-16α-methylpregna-1,4-diene-3,20-dione-21-thiol (1.00 gm) and N-formyl-L-methionine (1.30 gm) in the same manner as in Synthetic Example 1.

NMR (DMSO-d$_6$)δ; 0.78 (d, 3H, J=7Hz), 0.87 (s, 3H), 1.02–3.01 (m, 15H), 1.49 (s, 3H), 2.05 (s, 3H), 3.81 (d, 1H, J=18Hz), 4.16 (s, 1H), 4.24 (d, 1H, J=18Hz), 4.64 (m, 1H), 5.24 (s, 1H), 5.36 (s, 1H), 6.01 (s, 1H), 6.23 (d, 1H, J=10Hz), 7.30 (d, 1H, J=10Hz), 8.19 (s, 1H), 8.83 (d, 1H, J=7Hz).

IRνmax (cm$^{-1}$); 3384, 2932, 1664, 1622, 1524, 1456, 1396, 1300, 1068, 896, 706.

Synthetic Example 6

6,9-Difluoro-21-[2-(formylamino)-4-methylthio-1-oxobutylthio]-11α,17-dihydroxy-16α-methylpregna-1,4-diene-3,20-dione (Compound No. 5)

The title compound (0.027 gm) was prepared from 6,9-difluoro-11β,17-dihydroxy-16β-methylpregna-1,4-diene-3,20-dione-21-thiol (0.06 gm) and (N-formyl-L-methionine (0.175 gm) in the same manner as in Synthetic Example 1.

NMR (DMSO-d$_6$)δ; 0.79 (d, 3H, J=7Hz), 0.86 (s, 3H), 0.93–3.03 (m, 14H), 1.49 (s, 3H), 2.05 (s, 3H), 3.81 (d, 1H, J=18Hz), 4.16 (s, 1H), 4.24(d, 1H, J=18Hz), 4.56–4.72 (m, 1H), 5.29 (s, 1H), 5.47 (s, 1H), 6.10 (s, 1H), 6.29 {d, 1H, J=10Hz), 7.27 (d, 1H, J=10Hz), 8.18 (s, 1H), 8.83 (d, 1H, J=8Hz) IRνmax (cm$^{-1}$); 3368, 2932, 1668, 1634, 1526, 1456, 1392, 1298, 1068, 900, 708.

Synthetic Example 7

9-Fluoro-21-[2-(formylamino)-4-methylthio-1-oxobutylthio]-11β-hydroxy-16β-methyl-17-(1-oxopentyloxy)-pregna-1,4-diene-3,20-dione (Compound No. 6)

The title compound (1.03 gm) was prepared from 9-fluoro-11-hydroxy-16β-methyl-17-(1-oxopentyloxy)-pregna-1,4-diene-3,20-dione-21-thiol (4.80 gm) and N-formyl-L-methionine (6.15 gm) in the same manner as in Synthetic Example 1.

NMR (CDCl$_3$)δ; 0.90–2.73 (m, 18H), 0.92 (t, 3H, J=7Hz), 0.95 (s, 3H), 1.33 (d, 3H, J=7Hz), 1.58 (s, 3H), 2.11 (s, 3H), 2.42 (t, 2H, J=7Hz), 3.40 (d, 1H, J=15Hz), 3.87 (s, 1H), 3.99 (d, 1H, J=15Hz), 4.41 (m, 1H), 4.74 (m, 1H), 6.14 (s, 1H), 6.35 (dd, 1H, J=1.6, 10Hz), 7.34 (d, 1H, J=10Hz), 7.71 d, 1H, J=7Hz), 8.27 (s, 1H).

IRνmax (cm$^{-1}$); 3370, 2932, 1731, 1668, 1626, 1524, 1455, 1395, 1356, 891, 756.

Synthetic Example 8

21-[2-(Formylamino)-4-methylthio-1-oxobutylthio]-11β,17-dihydroxy-pregna-4-ene-3,20-dione (Compound No. 7)

The title compound (0.38 gm) was prepared from 11β,17-dihydroxy-pregna-4-ene-3,20-dione-21-thiol (1.00 gm) and N-formyl-L-methionine (1.41 gm) in the same manner as in Synthetic Example 1.

NMR (DMSO-d$_6$)δ; 0.75 (s, 3H), 0.86–2.67 (m, 21H), 1.36 (s, 3H), 2.05 (s, 3H), 3.79 (d, 1H, J=18Hz), 4.24 (d, 1H, J=18Hz), 4.30 (s, 1H), 4.31 (s, 1H), 4.62 (m, 1H), 5.46 (s, 1H), 5.56 (s, 1H), 8.18 (s, 1H), 8.84 (d, 1H, J=8Hz).

IRνmax (cm$^{-1}$); 3422, 2920, 1659, 1521, 1442, 1389, 1271, 1059, 866, 716.

Synthetic Example 9

9-Fluoro-21-[2-(formylamino)-4-methylthio-1-oxobutylthio]-11β-hydroxy-16β-methyl-17-(1-oxopropyloxy)-pregna-1,4-diene-3,20-dione (Compound No. 8)

The title compound (0.47 gm) was prepared from 9-fluoro-11 hydroxy-16β-methyl-17-(1-oxopropyloxy)-pregna-1,4-diene-3,20-dione-21-thiol (0.80 gm) and N-formyl-L-methionine (0.99 gm) in the same manner as in Synthetic Example 1.

NMR (DMSO-d$_6$)δ; 0.84 (s, 3H), 1.02 (t, 3H, J=8Hz), 1.13–2.86 (m, 17H), 1.23 (d, 3H, J=7Hz), 1.49 (s, 3H), 2.05 (s, 3H), 3.60 (d, 1H, J=17Hz), 3.74 (d, 1H, J=17Hz), 4.22 (br.s, 1H), 4.63 (m, 1H), 5.49 (s, 1H), 6.02 (s, 1H), 6.24 (dd, 1H, J=1.5, 10Hz), 7.30 (d, 1H, J=10Hz), 8.19 (s, 1H), 8.88 (d, 1H, J=8Hz).

IRνmax (cm$^{-1}$); 3376, 2940, 1732, 1668, 1624, 1520, 1456, 1396, 1357, 898, 760.

Synthetic Example 10

21-[2-(acetylamino)-4-methylthio-1-oxobutylthio]-9-fluoro-11,17-dihydroxy-16β-methylpregna-1,4-diene-3,20-dione (Compound No. 9)

The title compound (0.38 gm) was prepared from 9-fluoro-11β,17-dihydroxy-16β-methylpregna-1,4-diene-3,20-dione-21-thiol (0.50 gm) and N-acetyl-L-methionine (0.70 gm) in the same manner as in Synthetic Example 1.

NMR (DMSO-d$_6$)δ; 0.85–2.47 (m, 15H), 0.92 (s, 3H), 0.99 (d, 3H, J=7Hz), 1.49 (s, 3H), 1.93 (s, 3H), 2.04 (s, 3H), 3.91 (d, 1H, J=18Hz), 4.14 (d, 1H, J=18Hz), 4.18 (s, 1H), 4.49 (m, 1H), 5.28 (s, 1H), 5.47 (s, 1H), 6.01 (s, 1H), 6.22 (d, 1H, J=10Hz), 7.29 (d, 1H, J=10Hz), 8.59 (d, 1H, J=8Hz).

IRνmax (cm$^{-1}$); 3420, 2940, 1720, 1700, 1664, 1622, 1532, 1454, 1300, 1048, 894, 708.

Synthetic Example 11

21-[2-(t-butoxycarbonylamino)-4-methylthio-1-oxobutylthio]-9-fluoro-11β,17-dihydroxy-16β-methylpregna-1,4-diene-3,20-dione (Compound No. 10)

The title compound (1.50 gm) was prepared from 1.20 gm of 9-fluoro-11β,17-dihydroxy-16β-methylpregna-1,4-diene-3,20-dione-21-thiol and 2.20 gm of N-(t-butoxycarbonyl)-L-methionine in the same manner as in Synthetic Example 1.

NMR (CDCl$_3$)δ; 0.76–2.79 (m, 16H), 1.06 (s, 3H), 1.12 (d, 3H, J=7Hz), 1.46 (s, 9H), 1.55 (s, 3H), 2.12 (s, 3H), 3.05 (s, 1H), 3.91 (d, 1H, J=16Hz), 4.03 (d, 1H, J=16Hz), 4.36 (d, 1H, J=9Hz), 4.51 (m, 1H), 5.30 (d, 1H, J=9Hz), 6.12 (s, 1H), 6.33 (dd, 1H, J=1.5, 9Hz), 7.25 (d, 1H, J=9Hz).

IRνmax (cm⁻¹); 3454, 2944, 1698, 1668, 1623, 1515, 1455, 1395, 1374, 1299, 1251, 1167, 1098, 1047, 1005, 981, 894, 780.

Synthetic Example 12

9-Fluoro-21-(2-formylamino-1-oxobutylthio)-11β,17-dihydroxy-16β-methylpregna-1,4-diene-3,20-dione (Compound No. 11)

The title compound (0.28 gm) was prepared from 9-fluoro-11β,17-dihydroxy-16β-methylpregna-1,4-diene-3,20-dione-21-thiol (0.5 gm) and N-formyl-L-methionine (0.76 gm) in the same manner as in Synthetic Example 1.

NMR (DMSO-d₆)δ; 0.86 (t, 3H, J=6Hz), 0.93 (s, 3H), 1.00 (d, 3H, J=7Hz), 1.08-2.73 (m, 17H), 1.50 (s, 3H), 3.92 (d, 1H, J=18Hz), 4.16 (d, 1H, J=18Hz), 4.18 (br. s, 1H), 4.44 (m, 1H), 5.25 (s, 1H), 5.44 (s, 1H), 6.01 (s, 1H), 6.21 (d, 1H, J=10Hz), 7.29 (d, 1H, J=10Hz), 8.17 (s, 1H), 8.77 (d, 1H, J=8Hz).

IRνmax (cm⁻¹); 3416, 2952, 1740, 1700, 1666, 1622, 1518, 1456, 1394, 1046, 892.

Synthetic Example 13

21-[2-(acetylamino)-3-etylthio-1-oxopropylthio]-9-fluoro-11β,17-dihydroxy-16β-methylpregna-1,4-diene-3,20-dione (Compound No. 12)

The title compound (0.21 gm) was prepared from 9-fluoro-11 ,17-dihydroxy-16β-methylpregna-1,4-diene-3,20-dione-21-thiol (0.5 gm) and N-acetyl-S-ethylcysteine (0.70 gm) in the same manner as in Synthetic Example 1.

NMR (DMSO-d₆)δ; 0.93 (s, 3H), 1.00 (d, 3H, J=7Hz), 1.08-3.00 (m, 15H), 1.17 (t, 3H, J=7Hz), 1.50 (s, 3H), 1.95 (s, 3H), 3.95 (d, 1H, J=18Hz), 4.182 (d, 1H, J=18Hz), 4.185 (br. s, 1H), 4.56 (m, 1H), 5.26 (s, 1H), 5.45 (s, 1H), 6.00 (s, 1H), 6.22 (d, 1H, J=9Hz), 7.28 (d, 1H, J=9Hz), 8.68 (d, 1H, J=8Hz).

IRνmax (cm⁻¹); 3336, 2932, 1700, 1685, 1628, 1576, 1440, 1312, 1246, 1090, 894, 642.

Synthetic Example 14

17-acetoxy-9-fluoro-21-[2-(formylamino)-4-metylthio]-11β-hydroxy-16β-methylpregna-1,4-diene-3,20-dione (Compound No. 13)

The title compound (1.54 gm) was prepared from 17-acetoxy-9-fluoro-11β-hydroxy-16β-methylpregna-1,4-diene-3,20-dione-21-thiol (4.10 gm) and N-formyl-L-methionine (4.46 gm) in the same manner as in Synthetic Example 1.

NMR (CDCl₃)δ; 0.89-2.78 (m, 14H), 0.94 (s, 3H), 1 33 (d, 3H, J=7Hz), 1.57 (s, 3H), 2.13 (s, 3H), 2.17 (s, 3H), 3.40 (d, 1H, J=15Hz), 3.50 (s, 1H), 4.02 (d, 1H, J=15Hz), 4.37 (m, 1H), 4.74 (m, 1H), 6.13 (s, 1H), 6.34 (dd, 1H, J=2, 9Hz), 7.15 (d, 1H, J=7Hz), 7.29 (d, 1H, J=9Hz), 8.26 (s, 1H).

IRνmax (cm⁻¹); 3406, 2938, 1734, 1705, 1668, 1626, 1455, 1245, 891.

Synthetic Example 15

9-Fluoro-21-[2-(formylamino)-4-metylthio-1-oxobutylamino]-11β-17-dihydroxy-16β-methylpregna-1,4-diene-3,20-dione (Compound No. 14)

The title compound (0.91 gm) was prepared from 21-amino-9-fluoro-11β,17-dihydroxy-16β-methylpregna-1,4-diene-3,20-dione (1.00 gm) and N-formyl-L-methionine (0.98 gm) in the same manner as in Synthetic Example 1.

NMR (DMSO-d₆)δ; 0.94 (s, 3H), 1.03 (d, 3H, J=7Hz), 1 10-2.92 (m, 15H), 1.50 (s, 3H), 2.06 (s, 3H), 3.90-4.34 (m, 3H), 4.50 (m, 1H), 5.28 (s, 1H), 5.30 (s, 1H), 6.01 (s, 1H), 6.22 (d, 1H, J=10Hz), 7.30 (d, 1H, J=10Hz), 7.97-8.10 (m, 1H), 8.04 (s, 1H), 8.30 (d, 1H, J=8Hz).

IRνmax (cm⁻¹); 3384, 2936, 1726, 1700, 1662, 1624, 1534, 1392, 1248, 1048, 890.

Experimental Example 1

Anti-inflammatory activity and local side-effects were tested according to the following test procedures. The results are shown in Tables 1, 2, and 3.

Test Method of Anti-inflammatory Activity (1)

Samples containing Compound Nos. 1, 3, and 5 of the present invention and, as a comparative drug, betamethasone 17-valerate, at a concentration of $10^{-3}$ M each, were prepared using, an inflammation-inducing base material, as a mixture consisting of croton oil, ether, pyridine, and water (5:70:20:5). Wistar male rats, age 5 weeks, each group consisting of 5, were served for the test. The test samples and an inflammation-inducing base material (control) were infiltrated into circular felts (each 400 μl/felt) fixed onto specially prepared tweezers and the right auricles of the animals were put between the tweezers to apply the samples (800 μl/auricle) for 15 seconds at a constant pressure of 500 gw. After 6 hours, the both auricles were punched (φ 9 mm) and weighed.

An edema inhibitory rate determined by the following equation was taken as an index of the anti-inflammatory activity of the steroid samples.

$$\text{Edema inhibitory rate } (\%) = 100 - Y/Z \times 100$$

wherein Y is the weight difference (mg) of the right auricle to which the sample drug was applied and the untreated left auricle, and Z is the weight difference (mg) of the right auricle of the rat to which the inflammation-inducing base material was applied and the untreated left auricle.

The results are presented in Table 1.

TABLE 1

| Samples | Edema inhibitory rate (%) |
|---|---|
| Compound No. 1 | 44 |
| Compound No. 3 | 74 |
| Compound No. 5 | 74 |
| Betamethasone 17-valerate | 34 |

Table 1 shows superior anti-inflammatory activities of the steroid compounds of the present invention.

Test Method of Anti-inflammatory Activity (2)

Wistar male rats, age 5 weeks, each group consisting of 5-8 rats, were served for the test. Ethanol solutions of samples, Compound Nos. 1 and 6 of the present invention and, as a comparative drug, betamethasone 17-valerate, at a concentration of $10^{-2}$ M each, were infiltrated into antibiotic test filter paper (50 μl/paper) and dried. The paper was embedded into the right back of the rats. Into the left back was embedded an untreated antibiotic test filter paper. After 6 days, the animals were sacrificed by bleeding and the backs were incised to extract each granuloma formed around the filter. The granuloma was dried and weighed. To the right backs of the control group antibiotic test filter papers infiltrated with 50 μl/paper of ethanol and dried were embedded. The results are shown in Table 2.

TABLE 2

| Samples | Dry weight of ganuloma (mg) | Granulating Inhibitory Rate (%) |
|---|---|---|
| Compound No. 1 | 10.7 | 47.7 |
| Compound No. 6 | 7.4 | 63.9 |
| Betamethasone 17-valerate | 15.0 | 26.6 |
| Control | 20.4 | — |

Table 2 demonstrates excellent anti-inflammatory activities of the steroid compounds of the present invention.

Test Method of Local Side-effect Evaluation ddY male mice, weighing about 30 gm, each group consisting of 8-9, were served for the test. 100 μl of solutions of test compounds and the comparative drug (hydrocortisone) at a concentration of $5 \times 10^{-3}$ M in an ethanol-propylene glycol (7:3) mixture were applied to right side of the hair-cut abdomen of the mice on the next day of the hair-cut (the 1st day). Only the ethanol-propylene glycol (7:3) mixture was applied to the mice of the control group. The application was performed every day until the 14th day, excepting the 4th, 5th, 11th, and 12th days. On the day the hair was cut (the 0 day), and the 3rd, 7th, 10th and 14th days, the double-folded skin thickness of the animals on the right and left abdomens was measured by a gauge. The animals were bred separately in an individual cage during the test period. The results are shown in Table 3.

TABLE 3

| Differences in the thickness of the skin of right and left abdomens (Means ± S.E.) | | | | | |
|---|---|---|---|---|---|
| (Untreated skin thickness) − (Treated skin thickness) (mm) | | | | | |
| | 0 Day | 3rd Day | 7th Day | 10th Day | 14th Day |
| Control Group | −0.01 | 0.01 | 0.03 | 0.03 | −0.02 |
| Compound No. 1 | −0.01 | −0.01 | 0.01 | 0.00 | −0.03 |
| Hydrocortisone | −0.02 | −0.05* | 0.07 | 0.06 | 0.12** |

*$P < 0.05$ for Control
**$P < 0.01$ for Control

The results shown in Table 3 indicates that the compound of the present invention exhibits a smaller side effect than the comparative compound and is safer when applied to the skin or the like.

Experimental Example 2

Anti-allergic activity of the steroid compound of the present invention was tested according to the following test procedures.

Test Method of Anti-allergic Activity

Figure 1:
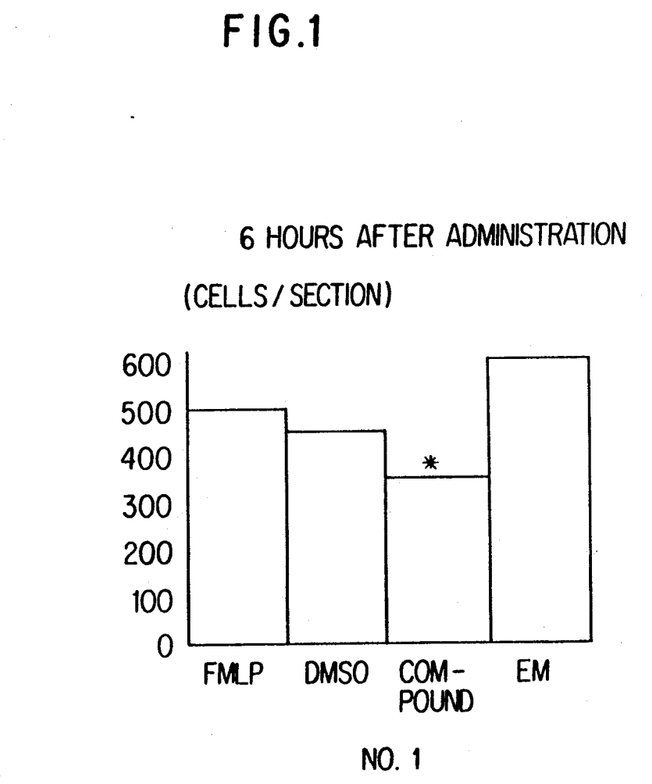
FIGS. 1 and 2 are graphs showing the eosinophiles infiltration inhibitory effect, which is an indicator of the anti-allergic activities, of the steroid compound of the present invention obtained from the experiment using guinea pigs.
Figure 2:
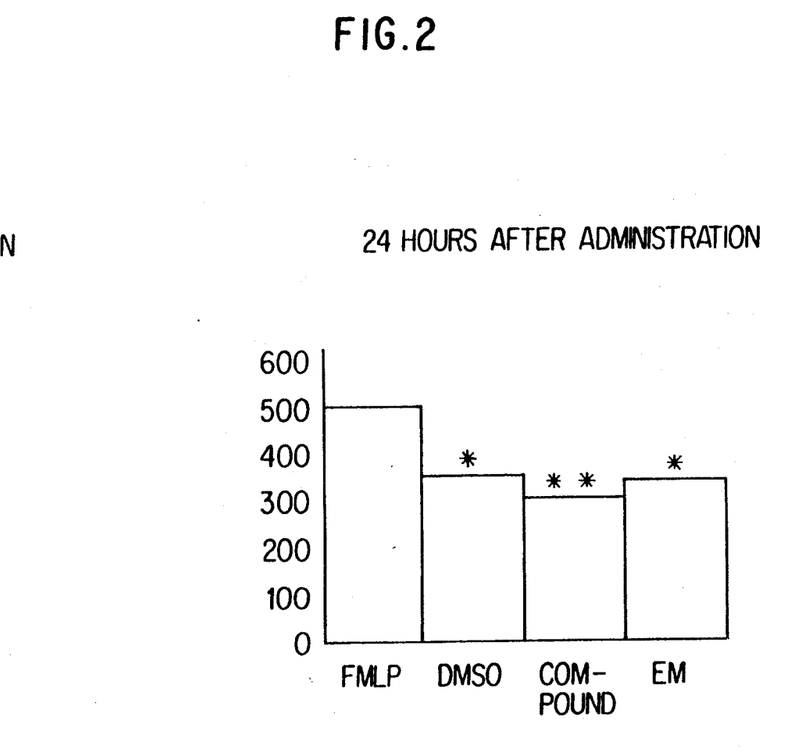

To tracheas around the neck of guinea pigs (male; weight 200-300 gm) exposed under anesthesia with Nembutal (0.05 ml/animal, i.p.) were injected FMLP ($10^{-4}$ M), which is an inflammation-inducing compound, dissolved in 1% dimethylsulfoxide solution in physiological saline, individually o together with the test compound with a 26 guage needle. For the negative control, only dimethylsulfoxide was injected, and for the positive control betamethasone was administered. After 6 or 24 hours, the animals were sacrificed with bleeding to extract tracheas, which was fixed in a 10% phosphate buffered formalin for longer than 24 hours. Eosinophiles infiltrated into the upper, middle, and lower parts of the trachea were counted by microscope. Numbers of eosinophiles found in tracheas to which the test compound was injected were compared with those to which FMLP was independently injected. The results are shown in FIGS. 1 and 2, in which the steroid compound of formula (I) is shown to exhibit a significant eosinophiles infiltration inhibitory effect both 6 and 24 hours after the administration, whereas betamethasone which is the positive control exhibited only a small effect after 4 hours.

The above results are the evidences that the steroid compound of the present invention is effective to the treatment of asthma, allergic rhinitis, eye diseases, e.g. conjunctival inflammation, and the like which are caused by the eosinophiles infiltration.

Experimental Example 3

Anti-rheumatism activity of the steroid compound of the present invention was tested according to the following test procedures. The inhibitory effect of interleukin 1 (IL-1) production, which is a cause of the rheumatism and worsens the disease, was determined and taken as an index of antirheumatism activity.

Method of the Determination of Interleukin 1 Production Inhibitory Effect

Figure 3:
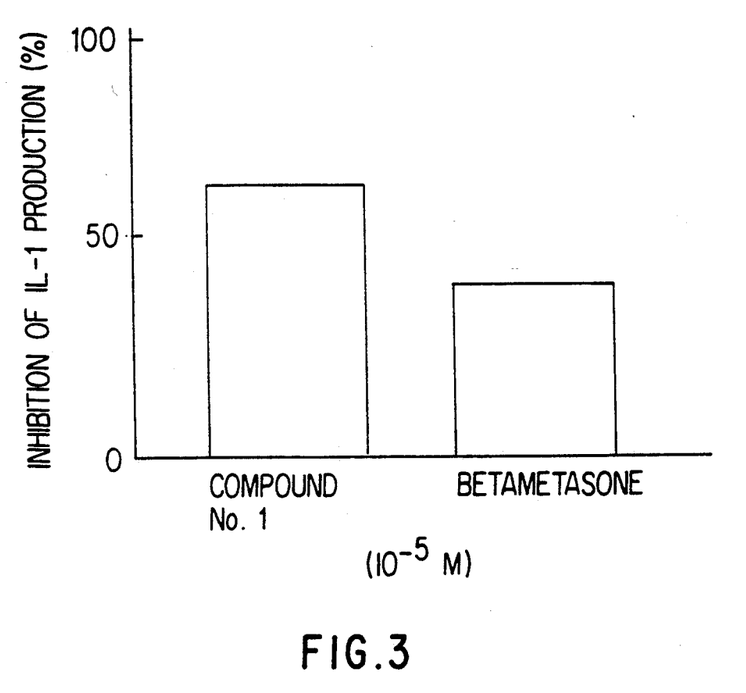
FIG. 3 is a graph showing the interleukin-1 production inhibitory effect, which is an indicator of the anti-rheumatism activities, of the steroid compound of the present invention obtained from the experiment using guinea pigs.

Guinea pig neutrophils induced by the intraperitoneal administration of 12% proteose pepton were cultured in the medium containing $10^{-5}$ M test compound. After removing the test compound by dialysis, the IL-1 activity of the supernatant of the culture broth was determined using the thymocyte growth activity as an index. The results are shown in FIG. 3, which demonstrates that the steroid compound of formula (I) effectively inhibits the IL-1 production which is an important cause of the rheumatism, thus evidencing that the compound is effective as an antirheumatism drug.

Experimental Example 4

Systemic side effects of the compound of the present invention were evaluated according to the following method.

Suspensions of the test compounds (2 mM) in peanut oil were subcutaneously injected into the back of ddY male mice (weight: about 30 gm), 10 mice consisting of a test group, two times, once a day at a 24 hour interval. After 24 hours from the last injection, the mice were sacrificed to extract the thymus and to weigh its weight. For the control group only peanut oil was administered. The results are shown in

TABLE 4

| | (Means ± S.E.) | |
|---|---|---|
| Samples | Initial body weight (gm) | Thymus weight/10 gm body weight (mg) |
| Control | 29.9 ± 0.1 | 24.4 ± 1.7 |
| Betamethasone | 29.5 ± 0.5 | 15.4 ± 1.4 |
| Hydrocortisone | 23.9 ± 0.5 | 20.8 ± 2.1 |
| Compound No. 1 | 29.3 ± 0.5 | 23.4 ± 0.3 |

Table 4 demonstrates that the steroid compound of formula (I) does not affect the weight of the thymus, thus exhibiting a smaller side effect on the thymus than betamethasone and hydrocortisone.

Experimental Example 5

Acute toxicity (oral administration) of the compound of the present invention was evaluated according to the following method.

Suspensions of the test compounds (Concentration: 30 mg/0.5 ml, 75 mg/0.5 ml, and 150 mg/0.5 ml) in olive oil (the Japanese Pharmacopeia) were administered to ICR mice (male, 5 weeks), fasted for 24 hours, by sonde in an amount of 500 μl/body. The viability on 14 days after the administration are shown in Table 5.

TABLE 5

| | Compound No. 1 | | | Betamethasone 17-valerate | | |
|---|---|---|---|---|---|---|
| Dose (mg/kg) | 5 | 3.3 | 1.7 | 5 | 3.3 | 1.7 |
| Viability (%) | 100 | 100 | 100 | 50 | 100 | 100 |

Preparation Example 1 <Liquid Preparation>

| | |
|---|---|
| Compound No. 1 | 0.1 gm |
| Propylene glycol | 30.0 ml |

The above components were dissolved in ethanol to make the total volume to 100.0 ml.

Preparation Example 2 <Oil Preparation>

| | |
|---|---|
| Compound No. 1 | 0.5 gm |
| Olive oil | 99.5 gm |

An oil preparation was prepared by blending the above components according to a conventional manner.

Preparation Example 3 <Lotion>

| | |
|---|---|
| Compound No. 1 | 0.5 gm |
| Talk | 200.0 gm |
| Glycerol | 200.0 ml |
| Purified water | Balance |
| Total | 1,000.0 ml |

A lotion was prepared by blending the above components according to a conventional manner.

Preparation Example 4 <Liniment>

| | |
|---|---|
| Compound No. 3 | 0.2 gm |
| Tragacanth | 25.0 gm |
| CMC-Na | 20.0 gm |
| Ethanol | 100.0 ml |
| Glycerol | 30.0 ml |
| Purified water | Balance |
| Total | 1,000.0 gm |

A liniment was prepared by blending the above components according to a conventional manner.

Preparation Example 5 <Oily Ointment>

| | |
|---|---|
| Compound No. 3 | 2.0 gm |
| Glycerol | 50.0 gm |
| Beeswax | 230.0 gm |
| Olive oil | Balance |
| Total | 1,000.0 gm |

An oily ointment was prepared by blending the above components according to a conventional manner.

Preparation Example 6 <Hydrophilic Ointment>

| | |
|---|---|
| Compound No. 3 | 3.0 gm |
| Talc | 100.0 gm |
| Glycerol | 100.0 ml |
| CMC-Na | 0.8 gm |
| Bentonite | 20.0 gm |
| Purified water | 120.0 ml |
| Hydrophilic ointment base material | 500.0 gm |

A hydrophilic ointment composition was prepared by blending the above components according to a conventional manner.

Preparation Example 7 <Pasta Preparation>

| | |
|---|---|
| Compound No. 5 | 1.0 gm |
| Zinc stearate | 25.0 gm |
| Starch | 25.0 gm |
| Purified lanolin | Balance |
| Total | 100.0 gm |

A pasta preparation was prepared by blending the above components according to a conventional manner.

Preparation Example 8 <Cataplasm Preparation>

| | |
|---|---|
| Compound No. 5 | 0.3 gm |
| 10% Polyacrylic acid solution | 30.0 gm |
| Sodium polyacrylate | 4.0 gm |
| Glycerol | 34.0 gm |
| Potassium alum | 0.8 gm |
| Sodium edate | 0.2 gm |
| Surfactant | 3.0 gm |
| Purified water | Balance |
| Total | 100.0 gm |

A paste for the cataplasm preparation was prepared by blending the above components according to a conventional manner. Then, the paste was applied to non-woven or lint fabric to obtain a cataplasm preparation.

Preparation Example 9 <Nasal Drip>

| | |
|---|---|
| Compound No. 1 | 20.0 mg |
| Flon 11 | 1,000.0 mg |
| Flon 12 | 2,000.0 mg |
| Flon 14 | 940.0 mg |
| Oleic acid | 40.0 mg |

An nasel drip was prepared by blending the above components according to a conventional manner.

Preparation Example 10 <Inhalation Preparation>

| | |
|---|---|
| Compound No. 1 | 20.0 mg |
| Flon 11 | 1,000.0 mg |
| Flon 12 | 2,000.0 mg |
| Flon 14 | 940.0 mg |
| Sorbitan trioleate | 40.0 mg |

An inhalation preparation was prepared by blending the above components according to a conventional manner.

Preparation Example 11 <Tablet>

| | |
|---|---|
| Compound No. 1 | 10.0 mg |
| Crystalline cellulose | 50.0 mg |

| Preparation Example 11 <Tablet> | |
|---|---|
| Lactose | 100.0 mg |
| Magnesium stearate | 2.0 mg |
| Hydroxypropyl cellulose | 18.0 mg |
| Total | 180.0 mg |

Tablets were prepared from the above components according to a conventional manner. The tablets can be coated with film, if required.

| Preparation Example 12 <Capsules> | |
|---|---|
| Compound No. 2 | 10.0 mg |
| Lactose | 148.0 mg |
| Starch | 50.0 mg |
| Magnesium stearate | 2.0 mg |
| Total | 210.0 mg |

Hard capsules were prepared from the above components according to a conventional manner.

| Preparation Example 13 <Granules> | |
|---|---|
| Compound No. 3 | 10.0 mg |
| Lactose | 240.0 mg |
| D-Mannitol | 200.0 mg |
| Sodium carboxymethyl cellulose | 18.0 mg |
| Hydroxypropyl cellulose | 130.0 mg |
| Total | 600.0 mg |

Granules were prepared from the above components according to a conventional manner.

| Preparation Example 14 <Powders> | |
|---|---|
| Compound No. 4 | 10.0 mg |
| Lactose | 283.0 mg |
| D-Mannitol | 200.0 mg |
| Hydroxypropyl cellulose | 5.0 mg |
| Talc | 2.0 mg |
| Total | 500.0 mg |

A powder preparation was prepared from the above components according to a conventional manner.

| Preparation Example 15 <Injection> | |
|---|---|
| Compound No. 1 | 50.0 mg |
| Hydrogenated castor oil | 200.0 mg |
| Propylene glycol | 150.0 mg |
| Glucose | 100.0 mg |

The above components were dissolved in purified water to provide an injection fluid according to a conventional manner.

| Preparation Example 16 <Suppository> | |
|---|---|
| Compound No. 1 | 20.0 mg |
| Hard fat | 880.0 mg |
| Total | 900.0 mg |

The suppositories were prepared from the above components according to a conventional manner.

| Preparation Example 17 <Eye Drop Preparation> | |
|---|---|
| Compound No. 1 | 3.0 mg |
| Physiological saline | 1,000.0 mg |

An eye drop preparation was prepared by blending the above components according to a conventional manner.

Since 21-substituted steroid compounds of formula (I) of the present invention possess excellent antiinflammatory, anti-allergic and anti-rheumatic activities, they are useful for the prevention, cure, and treatment of contact dermatitis, atopic dermatitis, seborrheic dermatitis, eczema nummulare, neurodermitis circumscripta, housewive's eczema, prurigo, drug eruption, toxicodermia, psoriasis, pustular bacterid, lichen planus, lichen nitidus, pityriasis rubra pilaris, pityriasis rosea Gibert, erythema-group, erythroderma, discoid lupus erythematosus, pemphigus, pemphigoid, Duhring dermatitis herpetiformis, alopecia areata, vitiligo vulgaris, sarcoidosis, keloid, hypertrophic scar, dysadrenocorticism, hypoadrenalism, rheumatism, bronchial asthma, ulcerous intestinitis, allergic rhinitis, conjunctivitis, and the like. They exhibit a little side effect.

Obviously, numerous modifications and variations of the present invention are possible in light of the above teachings. It is therefore to be understood that within the scope of the appended claims, the invention may be practiced otherwise than as specifically described herein.

What is claimed is:

1. A 21-substituted steroid compound of formula (I), wherein $R^1$ is a hydrogen atom, a lower alkyl, lower alkenyl, lower alkoxy, or phenyl group, $R^2$ is a hydroxyl group or an acyloxy group having 1–6 carbon atoms, $R^3$ is a hydrogen atom or a lower alkyl group, or $R^2$ and $R^3$ may together form a lower alkylidenedioxy group, $X^1$ and $X^2$ may be the same or different and individually represents a hydrogen atom or a halogen atom, $Y^1$ and $Y^2$ may be the same or different and individually represents a methylene group or a sulfur atom, Z is a sulfur atom or an imino group, the wave line means that the configuration of $R^3$ may be of either α or β, and dotted line between the 1 and 2 position means that the bond may be the double bond.

2. A composition comprising an effective amount of the steroid compound defined in claim 1 and a pharmaceutically acceptable carrier.

3. A method for the treatment of an inflammation, which comprises administering an effective amount of the steroid compound define din claim 1 to the patient suffering from an inflammatory disease.

4. A method for the treatment of an inflammation, which comprises externally applying an effective amount of the steroid compound defined in claim 1 to the body parts of the patient suffering from an inflammatory disease.

5. A method for the treatment of allergic diseases, which comprises administering an effective amount of the steroid compound defined in claim 1 to the patient suffering from an allergic disease.

6. A method for the treatment of rheumatism, which comprises administering an effective amount of the steroid compound defined in claim 1 to the patient suffering from rheumatism.

7. A method for the treatment of eye diseases, which comprises administering an effective amount of the steroid compound defined in claim 1 to the eye of the patient suffering from an eye disease.

* * * * *